(12) United States Patent
Cree et al.

(10) Patent No.: US 7,204,907 B2
(45) Date of Patent: Apr. 17, 2007

(54) ABSORBENT DEVICE USING AN APERTURED NONWOVEN AS AN ACQUISITION DISTRIBUTION LAYER

(75) Inventors: James W. Cree, Chesterfield, VA (US); Lino Iulianetti, Torre dei Passeri (IT); Antonietta Splendiani, Pescara (IT)

(73) Assignee: Tredegar Film Products Corporation, Richmond, VA (US)

( * ) Notice: Subject to any disclaimer, the term of this patent is extended or adjusted under 35 U.S.C. 154(b) by 6 days.

(21) Appl. No.: 10/783,428

(22) Filed: Feb. 20, 2004

(65) Prior Publication Data

US 2005/0027270 A1    Feb. 3, 2005

Related U.S. Application Data

(63) Continuation-in-part of application No. 10/308,312, filed on Dec. 2, 2002, now Pat. No. 6,849,319.

(51) Int. Cl.
*A61F 13/15* (2006.01)
*B32B 37/00* (2006.01)

(52) U.S. Cl. ............... 156/253; 156/251; 156/222; 156/244.19; 156/308.4; 156/514; 156/515; 156/269; 83/30; 83/39; 264/156

(58) Field of Classification Search ........... 156/222, 156/244.19, 251, 253, 308.4, 514, 515, 269; 83/30, 39; 264/156
See application file for complete search history.

(56) References Cited

U.S. PATENT DOCUMENTS

| 5,188,625 | A | 2/1993 | Van Iten |
| 5,567,501 | A | 10/1996 | Srinivasan |
| 5,709,921 | A | 1/1998 | Shawver |
| 6,039,906 | A | 3/2000 | Sageser |
| 6,106,925 | A | 8/2000 | Palumbo |

FOREIGN PATENT DOCUMENTS

| EP | 0 165 807 A1 | * 12/1985 |
| GB | 2272917 A | 1/1994 |
| JP | 62109621 A | 5/1987 |
| JP | 06270340 | 9/1994 |
| JP | 06328600 | 11/1994 |
| JP | 06328601 | 11/1994 |
| JP | 10-80968 | * 3/1998 |

OTHER PUBLICATIONS

International Search Report of the Patent Cooperation Treaty for International Application No. PCT/US05/05558 dated Dec. 29, 2005.
Written Opinion of the International Searching Authority for International Application No. PCT/US05/05558 dated Dec. 29, 2005.

* cited by examiner

*Primary Examiner*—Linda Gray
(74) *Attorney, Agent, or Firm*—Troutman Sanders LLP

(57) ABSTRACT

A method of making a composite intermediate layer by forming a resilient three dimensional apertured formed film; forming a nonwoven web of fibers; joining the nonwoven web with the apertured formed film; and aperturing the joined nonwoven web and formed film to create large scale apertures in the joined nonwoven web and formed film.

10 Claims, 2 Drawing Sheets

ABSORBENT DEVICE USING AN APERTURED NONWOVEN AS AN ACQUISITION DISTRIBUTION LAYER

RELATED APPLICATION

This application is a continuation-in-part of U.S. patent application Ser. No. 10/308,312 filed on Dec. 2, 2002, now U.S. Pat. No. 6,849,319 issued Feb. 1, 2005.

TECHNICAL FIELD

This invention relates to absorbent articles, and more particularly to intermediate layers of absorbent articles.

BACKGROUND

Modern absorbent articles are typically comprised of four basic layers: a topsheet, an absorbent core, an intermediate layer between the topsheet and the absorbent core, and a backsheet opposite the topsheet. Several design criteria affect the choice of materials for these layers. Both nonwovens and apertured films are used as topsheets, each having advantages and disadvantages. Absorbent cores may be made of many different combinations of materials, including pulp and other fibrous materials as well as super absorbent particles or fibers. Backsheets are typically made of films; sometimes breathable materials may be used, but the primary concern is that the backsheet remain impervious to fluid leakage. Intermediate layers are a more recent addition to the absorbent article market.

In the past, absorbent articles may have contained nonwoven materials between the topsheet and the absorbent core to reduce rewet from the absorbent core to the surface. Recently, intermediate layers of three-dimensional formed film have proven exceptionally successful at preventing rewet as well as increasing strikethrough performance and masking performance.

SUMMARY

In an absorbent article having a topsheet and an absorbent core, a three-dimensional, apertured, non-woven material is positioned between the topsheet and the absorbent core to improve the strikethrough, rewet, and fluid distribution characteristics of the absorbent article. The three-dimensional, apertured, nonwoven material may be a single layer of nonwoven material, multiple layers of nonwoven material, or a layer of nonwoven material combined with an apertured film.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Definitions

Figure 1:
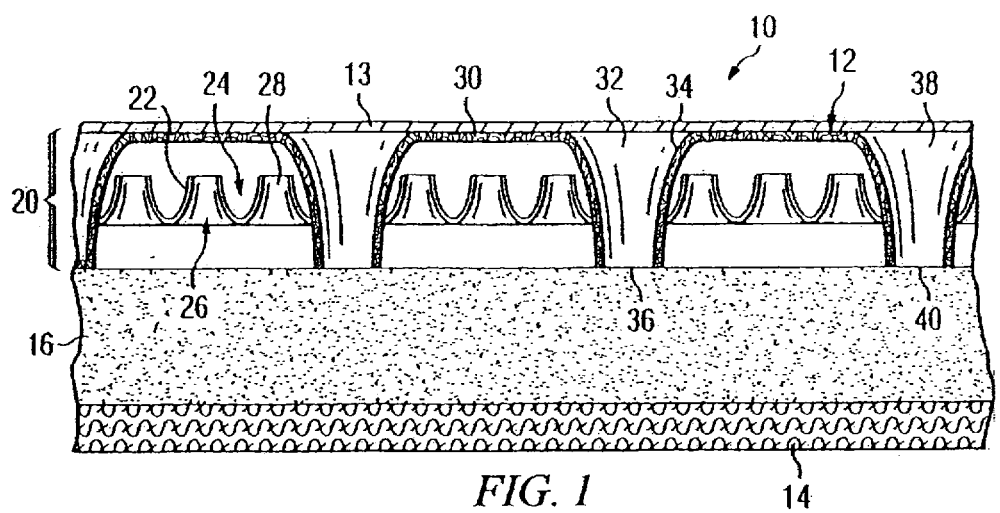
FIG. 1 is a cross sectional view of a first embodiment of the absorbent article of the invention.

As used herein, the term "substantially" means that a given property or parameter may vary by about 20% from the stated value.

As used herein, the term "absorbent article" means articles that absorb and contain body exudates. More specifically, the term refers to articles that are placed against or in proximity to the body of a wearer for absorbing and containing various exudates discharged from the body.

For example, "absorbent article", as used herein, includes diapers, incontinent articles, sanitary napkins, pantiliners, bandages, and other articles used to absorb body exudates.

The term "diaper" refers to a garment typically worn by infants and incontinent persons that is drawn up between the legs and fastened about the waist of the wearer. Examples of diapers from the prior art include diapers described in U.S. Pat. Re. No. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The term "incontinent article" refers to pads, undergarments, e.g., pads held in place by a suspension system, such as a belt, or other device, inserts for absorbent articles, capacity boosters for absorbent articles, briefs, bed pads, and similar devices, whether worn by adults or other incontinent persons. Examples of incontinent articles include those disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704, 115; 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et a. and Feist, et al. on Jan. 3, 1991.

The term "pantiliner" refers to absorbent articles that are less bulky than sanitary napkins that are generally worn by women between their menstrual periods. Examples of pantiliners are disclosed in U.S. Pat. No. 4,738,676 entitled "Pantiliner" issued to Osborn on Apr. 19, 1988.

The term "sanitary napkin" refers to an article that is worn by a female adjacent to the pudendal region that is intended to absorb and contain various exudates that are discharged from the body, e.g., blood, menses, and urine. Examples of sanitary napkins are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264, and 5,009,653 issued to Osborn on Aug. 21, 1990 and Apr. 23, 1991, respectively; and in U.S. patent application Ser. No. 07/605,583 filed Oct. 29, 1990 in the name of Visscher, et al.

Throughout this description, the expressions "topsheet" and "backsheet" denote the relationship of these materials or layers with respect to the absorbent core. It is understood that additional layers may be present between the absorbent core and the topsheet and backsheet, and that additional layers and other materials may be present on the side opposite the absorbent core from either the topsheet or the backsheet.

As used herein, the term "formed film" refers to a resilient three dimensionally formed film similar in structure to that produced by vacuum forming processes, as described in U.S. Pat. No. 4,456,570 to Thomas or U.S. Pat. No. 3,929,135 to Thompson, among others.

As used herein, the term "non-woven web" refers to a web that has a structure of individual fibers or threads that are interlaid, but not in any regular, repeating manner. Non-woven webs have been, in the past, formed by a variety of processes such as, for example, meltblowing processes, spunbonding process, and bonded carded web processes.

As used herein, the term "meltblown fibers", refers to fibers formed by extruding a molten thermoplastic material through a plurality of fine, usually circular, die capillaries as molten threads or filaments into a high velocity gas (e.g., air) stream that attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "stabilized" refers to a material of the present invention that is capable of being stored in a stable condition in any common or conventional web storage manner without the need for further heating or the additional of or joinder with other webs to stabilize the material. Such storage means would include for example, low tension rolls or festooned material in boxes.

As used herein, the term "melt-stabilized" refers to portions of a nonwoven web which have been subjected to localized heating and/or localized pressure to substantially consolidate the fibers of the nonwoven web into a stabilized film-like form.

As used herein, "pressure bonding" refers to a process in which a web is placed between two elements that exert pressure on the web to bind the various components of the web in the area where pressure is being exerted.

As used herein, the term "spunbonded fibers", refers to small diameter fibers that are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

The term "finished absorbent article" is used herein to generally mean any absorbent article having incorporated all layers of material and other features that the article is intended to have that affect the product's performance characteristics. This term includes, but is not limited to, products well known in the art as diapers, sanitary napkins, and adult incontinent briefs.

The term "insult" is used herein to refer to the act of applying a finite amount of liquid to the topsheet of a finished absorbent article. An insult may occur during product use and during finished product testing. Consequently, "multiple insults" occur when the same finished absorbent article is insulted more than once. Multiple insults may occur during product use and during finished product testing.

As used herein, "unconsolidated" means the fibers have some freedom of movement and are not fixed in position with respect to the other fibers in the web. In other words, the fibers generally are not compacted together or fused to the extent that an aperture cannot close, rather, the aperture may be blocked by some fiber strands that extend across, and partially obstruct it.

As used herein, "consolidated" means the fibers are generally compacted, fused, or bonded, so as to restrict movement of the fibers individually. Consolidated fibers will generally not extend out into an aperture and will likely be more dense than unconsolidated fibers.

As used herein "mesh count" means the number of holes per square centimeter. Therefore a material with a higher mesh would have more holes while a lower mesh would have fewer holes.

As used herein, the term "point bonding" means bonding one or more fabrics at a plurality of discrete points. For example, thermal point bonding generally involves passing one or more layers to be bonded between heated rolls, for example, an engraved pattern roll and a smooth calender roll. The engraved roll is patterned in some way so that the entire fabric is not bonded over its entire surface, and the calender roll is usually smooth. As a result, various patterns for engraved rolls have been developed for functional as well as aesthetic reasons.

As used herein, "gsm" is an abbreviation for grams per square meter.

Absorbent Article Embodiments

Referring to FIG. 1, FIG. 2, FIG. 3, and FIG. 5, absorbent article 10 has a body facing side 12. In use, the absorbent article 10 is typically placed so that body facing side 12 faces the user's body and the opposite side of the absorbent article is either exposed, as in a bandage, or faces the user's clothing, as in a diaper or feminine hygiene product. Topsheet 13 is positioned on the body facing side 12 of the absorbent article and comprises a fluid pervious material to allow fluids to enter the absorbent article 10. Both nonwovens and apertured films are typical materials used for topsheet 13. Backsheet 14 is opposite body facing side 12 and will typically be a fluid resistant or fluid impervious layer to prevent fluids from escaping the absorbent article 10. Absorbent core 16 will be between backsheet 14 and body facing side 12 to absorb fluids. Intermediate layer 20 will be between absorbent core 16 and body facing side 12. Intermediate layer 20 is designed to promote fluid flow from topsheet 13 to absorbent core 16 while also preventing fluid flow from absorbent core to topsheet 13, as discussed in the background and in the testing section below.

Figure 2:
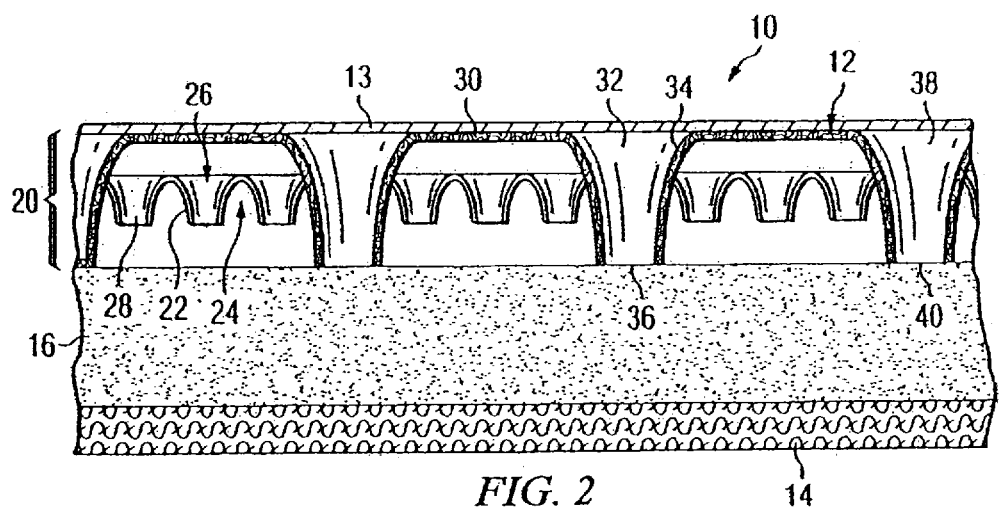
FIG. 2 is a cross sectional view of a second embodiment of the absorbent article of the invention.

In FIG. 1 and FIG. 2 the intermediate layer 20 has a resilient three dimensional formed film 22 with a male side 24 and a female side 26. Small scale apertures 28 in the formed film 22 have a mesh count of between about 20/cm$^2$ and 200/cm$^2$. More preferably the mesh count of the small scale apertures is between about 50/cm$^2$ and 100/cm$^2$. Most preferably the mesh count of the small scale apertures is about 90/cm$^2$. Formed film 22 is preferably made of a thermoplastic material to aid in forming. More preferably, formed film 22 is made of polypropylene, polyethylene, or some other polyolefin.

The resilient three-dimensional shape of the formed film 22 creates a void volume on both the male side and the female side of the formed film 22. It is advantageous in this invention to maintain that void volume and not allow the absorbent core 16 or the fibers from the nonwoven web 30 to fill the void volume. The void volume allows for efficient fluid transfer both above and below the formed film 22. Therefore a light tissue may be placed between the absorbent core and the intermediate layer 20 to help in maintaining void volume of the intermediate layer.

A nonwoven web 30 is attached to the formed film 22, between the formed film 22 and topsheet 13. Nonwoven web 30 is preferably comprised of fibers of polymeric material, although other fibers may be used. In particular, polypropylene and polyethylene, either alone or in bi-component and other blends, are effective.

A plurality of large scale apertures 32 extend through nonwoven web 30 and formed film 22. The large scale apertures 32 have a mesh that is less than the mesh of the small scale apertures 28. The mesh count of large scale apertures 32 will preferably be between $2/cm^2$ and $50/cm^2$, more preferably between $3/cm^2$ and $30/cm^2$, and most preferably between $6/cm^2$ and $11/cm^2$. Therefore, the small scale apertures 28 will be more numerous in a given area than the large scale apertures 32. An important aspect of the large scale apertures 32 is to provide a three-dimensional aspect to the intermediate layer 20.

In the preferred embodiments shown in FIG. 1 and FIG. 2, the large scale apertures are generally conical, having a larger opening 34 and a smaller opening 36. In particular, the larger opening 34 is between the body facing side 12 and the smaller opening 36. In a more preferred embodiment there are substantially unconsolidated fibers 38 near the larger opening and substantially consolidated fiber 40 near the smaller opening.

In the preferred embodiments shown in FIGS. 1 and 2, it is possible for the substantially consolidated fibers 40 and the formed film 22 to be fused to create a point bond between the nonwoven web 30 and the formed film 22 at a plurality of the large scale apertures 32.

In the preferred embodiment shown in FIG. 1, the male side 24 of the formed film 22 is facing the nonwoven web 30. In contrast, FIG. 2 shows an embodiment where the female side 26 of the formed film 22 is facing the nonwoven web 30.

In a preferred embodiment, the side of formed film 22 that is facing the nonwoven web 30, the male side 24 in FIG. 1 or the female side in FIG. 2, is treated with a surfactant, and therefore is more hydrophilic. Typical surfactants would include non-ionic and silicone based surfactants, although others may be used.

Figure 3:
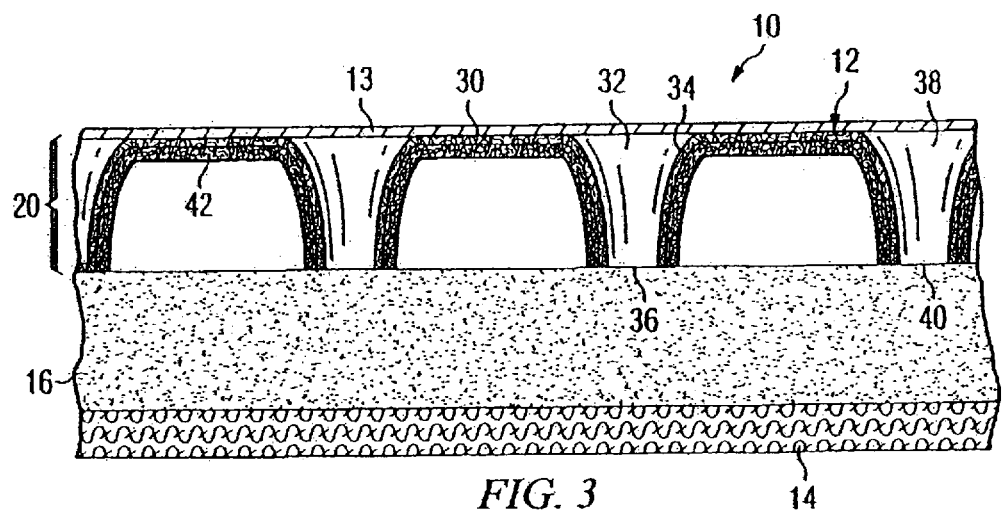
FIG. 3 is a cross sectional view of a third embodiment of the absorbent article of the invention.

As shown in FIG. 3, the intermediate layer 20 may include a stiffer nonwoven layer 42 in the place of formed film 22. The stiffer nonwoven layer 42 has a relatively rough texture, as compared to nonwoven web 30, and is formed of fibers with an average diameter larger than the fibers of nonwoven web 30. The stiffer nonwoven layer 42 is formed of materials similar to those used in nonwoven layer 30. The stiffer nonwoven layer 42 may be a separate nonwoven web joined with nonwoven web 30 in a manner similar to formed film 22, or it may be a layer of fibers formed with nonwoven web 30. The discussion above regarding the formation of large scale apertures 32 applies to the intermediate layer 20 of FIG. 3, with the stiffer nonwoven layer 42 replacing the formed film 22.

Figure 5:
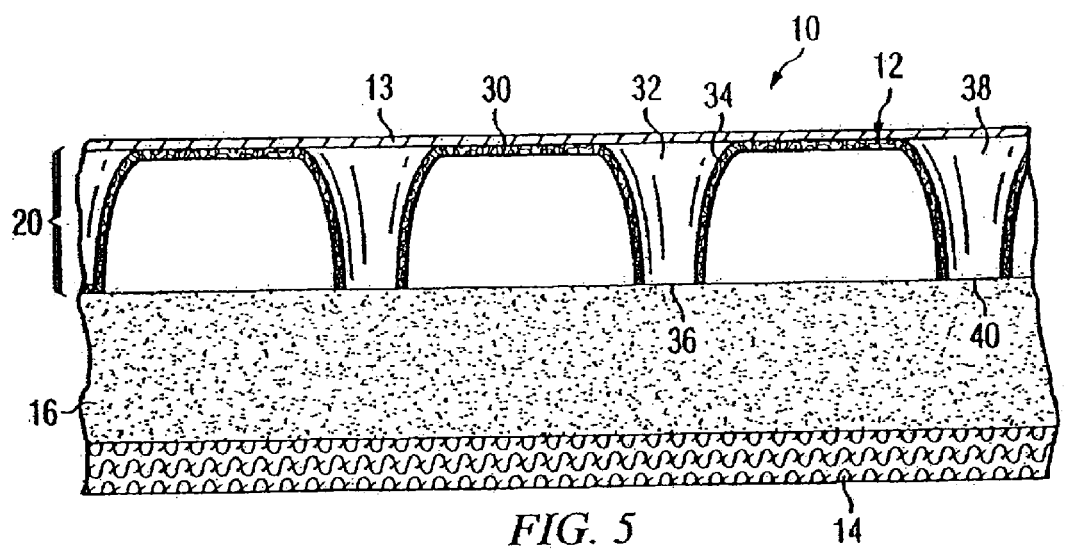
FIG. 5 is a cross sectional view of a fourth embodiment of the absorbent article of the invention.

FIG. 1, FIG. 2, and FIG. 3 show composite versions of intermediate layer 20. Each has a nonwoven web of fibers 30 and a stiffening means in the form of apertured film 22 or nonwoven layer 42. Other stiffening means may be selected from non-apertured films, less stiff nonwoven layers, woven layers, adhesive coatings, surfactant coatings, and other materials added to the nonwoven layer 30. In FIG. 5, intermediate layer 20 is comprised of nonwoven web 30 with large scale apertures 32, but without a stiffening means.

Method for Making Intermediate Layers

A formed film 22 is manufactured to have a resilient three dimensional structure. The film is preferably manufactured by a vacuum forming process, wherein a molten layer of thermoplastic material is fed from a melt die onto a shaped screen utilizing vacuum pressure to form the thermoplastic material to the shape of the screen. Other methods for manufacturing resilient three dimensional formed films may include reheat processes.

A nonwoven web 30 is manufactured from polymeric fibers. In a preferred embodiment the nonwoven web is airthrough bonded, carded thermobonded, spunbonded, or spunbond meltblown spunbond. In a preferred embodiment the fibers are single component or bi-component. In a preferred embodiment the material is polypropylene or polyethylene, although polyester may be added.

The formed film 22 and nonwoven web 30 are joined prior to forming of the large scale apertures 32. In a preferred embodiment the formed film 22 and the nonwoven web 30 are aligned adjacent each other. In another preferred embodiment the formed film 22 is adhesively secured to the nonwoven web 30 prior to the forming of large scale apertures 32. The importance of joining the nonwoven web 30 with the formed film 22 is so that large scale apertures 32 penetrate both the nonwoven web 30 and the formed film 22.

Figure 4:
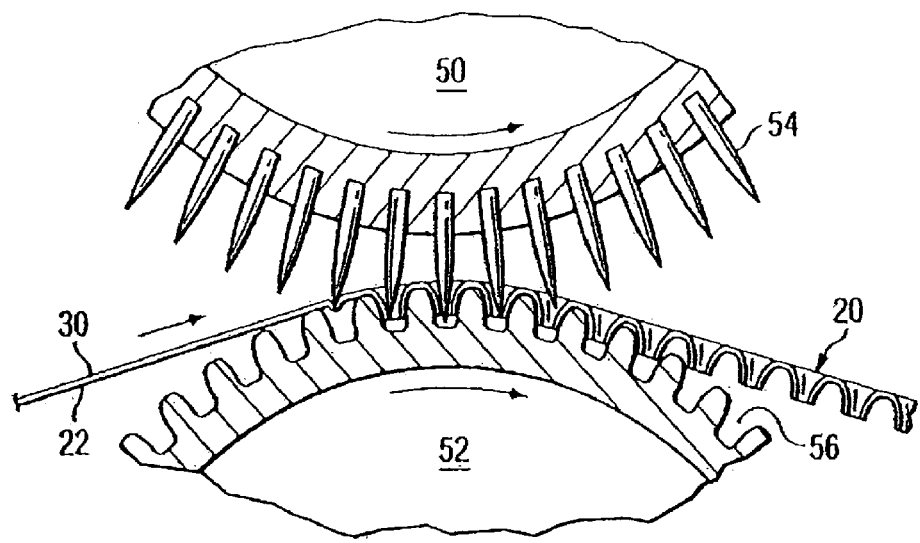
FIG. 4 is a cross sectional view of the method for manufacturing a composite topsheet.

FIG. 4 shows a preferred mechanism for forming large scale apertures 32. A pin roll 50 and counter roll 52 rotate in opposite directions to form a nip through which the nonwoven web 30 and formed film 22 are fed. Pins 54 protrude from the surface of pin roll 50. Holes 56 are recessed into counter roll 52. Pin roll 50 and counter roll 52 are aligned so that pins 54 mate with holes 56.

In a more preferred embodiment, pin roll 50 and counter roll 52 are manufactured of rigid material and are mounted on an adjustable chassis to allow modification of the distance between the rolls. In particular, pin roll 50 is preferably manufactured of metallic material and pins 54 are preferably manufactured of a metallic material. Pins 54 preferably have a pointed end and taper from about half of their length to the pointed end. In a preferred embodiment pins 54 are heated, as discussed in more detail below.

The holes 56 are preferably larger than pins 54 and are shaped. In a preferred embodiment the shape of holes 56 is partially replicated by the large scale apertures 32. In a preferred embodiment the holes 54 are generally conical so that when the pins 54 push material into holes 56 the material near the tips of pins 54 is compressed further than any other material, and experiences more heat transfer if the pins 54 are heated. This preferred combination of narrow heated pins 54 and generally conical holes 56 produces a preferred large scale aperture 32 having generally consolidated fibers 40 near a smaller opening 36 and generally unconsolidated fibers 38 near a larger opening 34.

In a less preferred embodiment counter roll 52 may be manufactured of a pliable material, thereby making holes 56 unnecessary. In such an embodiment pins 54 would simply protrude into the pliable material of counter roll 52.

The pins 54 may be heated for several reasons. One reason to heat pins 54 is to properly form large scale apertures 32. The heated pins 54 may also be heated to a temperature sufficient to bond the nonwoven web 30 to the formed film 22. Furthermore, the heated pins 54 may help in creating substantially consolidated fibers 40 near the smaller openings 36. The pins may also be heated to provide for structural resilience in large scale apertures 32 in order to maintain void volume between the intermediate layer 20 and the absorbent core 16. In particular, the heated pins may cause the formed film 22 or the stiffer nonwoven layer 42 to become more rigid and support the large scale apertures 32 during further processing, storage, or use. This allows the use of a softer nonwoven web 30 without compromising the shape of the large scale apertures 32 or the void volume they create between the intermediate layer 20 and the absorbent core 16.

In a first preferred embodiment the pins 54 are heated to a temperature sufficient to fuse the consolidated fibers 40 and the formed film 22 near the smaller openings 36, thus securing the nonwoven web 30 to the formed film 22. Even at this temperature, the shape of the pins 54 and the holes 56 is such that unconsolidated fibers 38 still exist near the large openings 34.

In another preferred embodiment, the nonwoven web 30 is comprised of materials with more than one melting point, such that a plurality of fibers have a melting point near the melting point of the material of formed film 22, and lower than other fibers in the nonwoven web 30.

The pins 54 are heated to a temperature to melt the lower melting point fibers and the formed film 22 near the smaller openings 36, thus forming consolidated fibers 40 and securing the nonwoven web 30 to the formed film 22.

In yet another embodiment the fibers of the nonwoven web 30 have a melting point that is higher than the melting point of the material of the formed film 22. The pins 54 are heated to a temperature sufficient to melt the formed film 22 and bond the consolidated fibers 40 near the smaller opening 36, thereby securing the nonwoven web 30 to the formed film 22.

In yet another embodiment the nonwoven web 30 is secured to the formed film 22 prior to forming the large scale apertures. Preferably the securing would be an adhesive bonding. In this embodiment the pins 54 are heated to a temperature sufficient to shape the nonwoven web 30 in the vicinity of the large scale apertures and form consolidated fibers 40 near the smaller opening 36, but not necessarily enough to fuse the consolidated fibers 40 to the formed film 22, or the formed film 22 to the nonwoven web 30.

In yet another preferred embodiment the formed film any of the above examples is replaced with a stiffer nonwoven layer 42 with similar material characteristics.

In yet another preferred embodiment the nonwoven web 30 is run through the pins discussed above without a stiffening means 22, 42.

Finished Article Testing

The performance of several preferred embodiments of intermediate layer 20 was evaluated in use on a Proctor & Gamble Petalo blu Core with an HFF topsheet. The preferred embodiments were compared against the performance of a Procter & Gamble acquisition distribution layer (ADL 70 gsm).

The three embodiments tested were Type 14, Type 15, and Type 16, described below:

Type 14 is a spunbond/meltblown/spunbond 15 gsm nonwoven combined with an air-through bonded 25 gsm nonwoven.

Type 15 is a carded thermal-bonded philic 18 gsm nonwoven combined with a Tredegar three-dimensional apertured formed film with the male side facing the topsheet.

Type 16 is a single layer of carded airthrough bonded philic 18 gsm nonwoven.

The following table summarizes the results of the tests for strikethrough, wetback, and partition coefficient. Both the strikethrough and the wetback are measured in accordance with the test method described below. Comparatively speaking, higher performance in both tests is achieved by a lower numerical result. In other words, the lower the amount of time required to absorb the fluid, the better the strikethrough performance, and the lower the amount of fluid that is collected at wetback, the better the wetback performance. Partition coefficient core is a measure of the percent of fluid retained in the absorbent core of the absorbent article after strikethrough and rewet testing as described in test method described below. A higher partition coefficient core is preferred as it indicates that the fluid is not being retained in the topsheet and ADL layers or being released as wetback.

| Intermediate Layer | Strikethrough (s) | Wetback (g) | Partition Coefficient Core (%) |
| --- | --- | --- | --- |
| P&G | 3.01 | 0.4 | 74 |
| Type 14 | 2.12 | 1.69 | 92 |
| Type 15 | 1.98 | 0.47 | 88 |
| Type 16 | 1.69 | 0.41 | 86 |

As can be seen, all of the materials tested had better strikethrough performance than the P&G ADL. Type 15 and type 16 had better wetback performance than the P&G ADL, as well. All of the tested materials had better partition coefficient core measures than the P&G ADL.

Strikethrough, Wetback and Partition Coefficient Test Method

The test method below is used to determine the acquisition time (strikethrough), the rewet performance (wetback) and fluid distribution (partition coefficient) of constructed feminine hygiene products.

In general terms, a feminine hygiene product is dismantled and weighed in each layer (topsheet, acquisition distribution layer (ADL) and absorbent core). The feminine hygiene product is reconstructed and insulted with 10 ml of saline solution. The strikethrough time is measured and recorded. After 20 minutes, 10 pre-weighted pick up papers are placed onto the insulted region and 0.58 psi of pressure is applied for 2 minutes. The pick-up papers are weighed again and the amount of rewet is calculated and reported in grams. The feminine hygiene product is dismantled again and the parts are weighed again to calculate the partition coefficient of each layer (% of liquid retained in each layer). Note that this test method is based on the following EDANA Recommended Test Methods: ERT 150.5-02 "Liquid Strike-Through Time" and ERT 151.3-02 "Wetback".

The following equipment is used in this test method:
50 ml capacity Burette with a supporting stand.
Strikethrough apparatus according to EDANA ERT 150.5-02 (including a funnel with magnetic valve, ring stand to support the funnel, strikethrough plate with electrodes, base plate, and electronic timer) sold under the name Lister by Lenzing Technik of Austria.
Pickup paper (ERT FF3—STRIKETHROUGH/WETBACK) supplied by Hollingworth & Vose Company Ltd. (UK).
Analytical balances (Accuracy of 0.001 g).
Weight of 4 Kg with a 100 mm×100 mm surface to provide 0.58 psi load.
Simulated menstrual fluid having a viscosity of 13 cps (centipoises)±1 cps as measured at 25° C. and containing the following ingredients listed as percentage by weight:
  90.37% Water ($H_2O$)
  7.50% Glycerin
  1.13% Sodium Carboxymethyl Cellulose (CMC)
  0.50% Sodium Chloride (NaCl)
  0.40% Sodium Hydrogen Carbonate ($NaHCO_3$)
  0.10% Ca24—a commercially available anti-bacterial agent, sourced from Maycos Italia.

It is recommended that the test be conducted in a standard laboratory environment with a temperature of 20° C.±2° C. and relative humidity of 50%±5%. The specimen and pick-up paper should be conditioned for 24 hours prior testing at 23° C.±2° C. and relative humidity of 50%±5%.

To begin testing, the feminine hygiene product is deconstructed. The topsheet, ADL and core (including the backsheet and other non-absorbent parts) are carefully detached from each other. The feminine hygiene product may be frozen to assist in separating the layers when hot melt adhesive was used in the original construction of the product. The test specimen should be clean and free of edge tear, wrinkles and blemishes, which can contribute to false results. After separation, weigh the topsheet and the ADL and record the weights as $T_o$ and $ADL_o$, respectively. Additionally, weigh the remaining part of the feminine hygiene product, including the core and backsheet and record the weight as $Core_o$. The feminine hygiene product is then carefully reconstructed to form an intact product.

Set up the ring stand holding the funnel and position the burette with the tip inside the funnel. Place the strikethrough plate on the feminine hygiene product with the product's acquisition side up and the center of the plate over the center of the product's insult point, near the middle of the product. Check that the electrodes in the strikethrough plate are clean. Adjust the height of the funnel to the top of the cavity in the plate. Ensure that the electrodes are connected to the timer. Activate the timer and set the time to zero. Fill the burette with the simulated menstrual fluid. Keep the discharge valve of the funnel closed and run 10 ml of simulated menstrual fluid from the burette to the funnel. Open the magnetic discharge valve of the funnel to discharge the 10 ml of simulated menstrual fluid. Record the strikethrough time as displayed by the timer. Gently remove the feminine hygiene product from the strikethrough apparatus and leave it in a horizontal position for 20 minutes to ensure even diffusion of the liquid.

Weigh 10 layers of dry pick-up paper, record the mass and place them over the insult point of the feminine hygiene product. Carefully apply the 4 kg weight onto the pick-up paper over the insulted point of the feminine hygiene product and leave it in place for 2 minutes. Remove the weight and reweigh the pick-up papers. Detach each layer (topsheet, ADL, and core, as above) and weigh them to record $T_{Fin}$, $ADL_{Fin}$ and $Core_{Fin}$, respectively. Repeat the test on at least two more feminine hygiene products.

For each feminine hygiene product, calculate the Rewet using the following formula:

Rewet $(g)$=[Wet Weight of pickup paper $(g)$–Dry Weight of pickup paper $(g)$]

Evaluate the Partition Coefficient of each layer using the following formula:

$$\text{Partition Coefficient Topsheet } (\%) = \frac{(T_{Fin} - T_o)}{(Liquid_{Discharged})} \times 100$$

$$\text{Partition Coefficient } ADL \ (\%) = \frac{(ADL_{Fin} - ADL_o)}{(Liquid_{Discharged})} \times 100$$

$$\text{Partition Coefficient Core } (\%) = \frac{(Core_{Fin} - Core_o)}{(Liquid_{Discharged})} \times 100$$

Where:

$Liquid_{Discharged} = $

Rewet + $(T_{Fin} - T_o)$ + $(ADL_{Fin} - ADL_o)$ + $(Core_{Fin} - Core_o)$

CONCLUSION

A number of embodiments of the invention have been described. Nevertheless, it will be understood that various modifications may be made without departing from the spirit and scope of the invention. For example, additional layers may be added to the absorbent article. Accordingly, other embodiments are within the scope of the following claims.

What is claimed is:

1. A method of making a composite intermediate layer comprising the steps of:
   providing a resilient three dimensional apertured formed film having a male side, a female side, and a mesh count;
   providing a nonwoven web of fibers;
   joining the nonwoven web with the apertured formed film; and
   aperturing the joined nonwoven web and formed film to create large scale apertures in the joined nonwoven web and formed film, a plurality of said large scale apertures created at a mesh count that is less than the mesh count of the apertures of the resilient three dimensional apertured formed film.

2. The method of claim 1 wherein the resilient three dimensional apertured formed film is formed by vacuum.

3. The method of claim 1 wherein the nonwoven web of fibers is formed by one of airthrough bonding, carded thermobonding, or spunbond meltblown spunbonding.

4. The method of claim 1 wherein the joining of the nonwoven web to the formed film includes the addition of an adhesive between the nonwoven web and the formed film.

5. The method of claim 1 wherein the aperturing of the joined nonwoven web formed film secures the nonwoven web to the formed film.

6. The method of claim 5 wherein the nonwoven web is secured to the formed film by the fusing of the fibers of the nonwoven web to portions of the formed film at the large scale apertures.

7. The method of claim 5 wherein the nonwoven web is secured to the formed film by the melting of the formed film near the large scale apertures.

8. The method of claim 5 wherein the nonwoven web is secured to the formed film by the melting of a plurality of the fibers in the nonwoven web near the large scale apertures.

9. The method of claim 1 wherein a large scale aperture is formed by a heated needle mating into a shaped recess such that the apertures are resilient and three dimensional.

10. The method of claim 9 wherein the large scale aperture is shaped by a contacting surface of the needle and the shaped recess such that the fibers of the nonwoven web are selectively fused only in the vicinity of the contacting surface.

* * * * *